United States Patent [19]

Voli

[11] Patent Number: 4,879,106

[45] Date of Patent: Nov. 7, 1989

[54] METHODS FOR TREATING GINGIVITIS AND PARADENTAL PYORRHEA

[76] Inventor: Giorgio Voli, No. 17, Lungotevere Prati, 00193 Roma, Italy

[21] Appl. No.: 19,558

[22] PCT Filed: Jul. 2, 1986

[86] PCT No.: PCT/IT86/00048

§ 371 Date: Jan. 27, 1987

§ 102(e) Date: Jan. 27, 1987

[87] PCT Pub. No.: WO87/00051

PCT Pub. Date: Jan. 15, 1987

[30] Foreign Application Priority Data

Jul. 2, 1985 [IT] Italy .............................. 48306-A/85

[51] Int. Cl.⁴ .......................... A61K 7/22; A61K 7/26; A61K 33/24; A61K 33/30
[52] U.S. Cl. ........................................ 424/54; 424/58; 424/195.1; 424/640; 424/641; 514/900; 514/901; 514/902
[58] Field of Search ...................... 424/145, 195.1, 58, 424/54; 514/900, 901, 902

[56] References Cited

U.S. PATENT DOCUMENTS 4,425,325 1/1984 Ritchey et al. ........................ 424/54

OTHER PUBLICATIONS

Martindale—The Extra Pharmacopoeia, The Pharmaceutical Press, Twenty-eighth Edition (1982) pp. 286, 496, 509, 510.

*Primary Examiner*—Douglas W. Robinson
*Assistant Examiner*—Joseph A. Lipovsky
*Attorney, Agent, or Firm*—Richard Bushnell

[57] ABSTRACT

A composition for preparing a medicament for topical treatment of paradentium diseases, said composition comprising the ammonium salt of sulfoichthyolic acid, zinc oxide, titanium dioxide and fluid extract of Hamamelis in a pharmaceutically acceptable carrier. Said composition is useful especially for treatment of gingivitis and alveolar pyorrhea.

6 Claims, No Drawings

METHODS FOR TREATING GINGIVITIS AND PARADENTAL PYORRHEA

The present invention relates to a composition for preparing a medicament for topical treatment of paradentium diseases. More particularly, the present invention relates to a pharmaceutical composition which is already known per se, and which has shown an unforeseeable and efficient activity in the medical treatment of diseases of the oral mucous membranes, especially in the treatment of gingivitis and alveolar pyorrhea.

As is well known, gingivitis is a general term comprising the inflammations of gums resulting from various causes, for instance from toxic, bacterial causes, from dyscrasia, from avitaminosis etc., which are supported and promoted by salivary tartar or by other constitutional factors.

The inflammatory or swollen state is generally concomitant with a high tendency to bleeding, which results from even very low traumatic causes, such as those due to the commonly performed hygienic care of the oral cavity.

The treatments which are generally recommended for gingivitis consist in the employment of special toothpastes, of mouth-washes or of liquid solutions for gums to be applied locally. None of the known products showed suitable to give a rapid and definitive solution to the problem of such diseases of paradentium, as they allow to obtain at most a temporary relief from the swollen or inflammatory state and from bleeding, and, in addition, repeated and constant applications of such products are necessary in most cases.

As is likewise already known, pyorrhea is a degenerative and inflammatory disease affecting teeth and paradentium, aetiology of such disease being not well known. Among the factors which originate the disease, a major importance seems to be ascribable to debilitating diseases, avitaminoses, metabolic and endocrine alterations.

According to the prevalence of the degenerative or of inflammatory phenomena, a purulent inflammatory and a necrotic-degenerative are distinguished. The first one is characterized by chronic putrefaction phenomena affecting the gums, the peridental tissues and the alveolar walls with the formation of pyorrhoic pockets or cavities from which a purulent material comes out. The gums show a tendency to become loose and teeth become increasingly unsteady till they are lost.

In the ischemic and degenerative form, which is called "dry pyorrhea", no alterations affect the gums, but an always increasing unsteadiness occurs of teeth till they are lost.

The medical treatment employed up to the present time consists in treating the general diseases possibly present, and in caring for a scrupulous hygiene of the mouth. Sometimes suitable prostheses are employed for keeping the teeth steady by linking the same to each other, or teeth are devitalized so as to cause the arthrosis of the dental alveolar articulation.

As a consequence, though some preparations are commercially available at the present time which are recommended as coadjuvant agents in the therapy of pyorrhea, no drugs exist which are able to cure such disease, and alveolar pyorrhea is considered as in incurable affection which very often makes it necessary to replace teeth by a dental prosthesis.

Thus, the object of the present invention is to provide a composition suitable to be employed for obtaining a medicament for treatment of pyorrhea, gingivitis, and in general of any affection of paradentium.

After different and ineffectual attempts, it was surprisingly discovered that a composition comprising the ammonium salt of sulfoichthyolic acid, zinc oxide and titanium dioxide, the fluid extract of Hamamelis and a pharmaceutically acceptable carrier caused a remarkably rapid and complete recovery of patients affected with various forms of paradentium diseases.

A composition of the kind mentioned above was already known but it has never been applied to the medical topical treatment of the affections of the oral mucous membrane, and it is to be remarked that the surprising specific efficiency of said composition, clearly observed and specified within the scope of the present invention, was really unforeseeable.

Though the active agent among all consituents of the composition of the present invention is supposed to be the ammonium salt of sulfoichthyolic acid, which has a notable keratoplastic and antiphlogistic activity, and a certain antiseptic power, the synergic effect of the other components, in particular of the Hamamelis extract, is also of a relevant importance as it exerts an astringent and vascoconstrictive action.

It is believed that the combined action of the ammonium salt of sulfoichthyolic acid and of the fluid extract of Hamamelis is the basis of the decongesting effect observed when applying the composition of the present invention to the swollen mucous membranes of gums.

Moreover, in the case of alveolar pyorrhea, it can be supposed that zinc oxide and titanium dioxide exert a cementing action whose effect is that of strengthening teeth within their alveoli.

The active components of the composition according to the present invention can be present in the following percentage amounts:

| | |
|---|---|
| ammonium sulfoichthyolate | 1–3% by wt. |
| zinc oxide | 5–20% by wt. |
| titanium dioxide | 3–9% by wt. |
| fluid extract of Hamamelis | 0.5–2% by wt. |

The pharmaceutically acceptable carrier (the excipient) employed for the preparation of drug consists preferably of anhydrous lanolin, white petrolatum, liquid paraffin, vanillin, French lavender and distilled water.

Such components are present by preference in percentage amounts which are variable within the following limits:

| | |
|---|---|
| anhydrous lanolin | 35–45% by wt. |
| white petrolatum | 10–20% by wt. |
| liquid paraffin | 10–20% by wt. |
| vanillin | 0–0.05% by wt. |
| essence of French lavender | 0–0.06% by wt. |
| distilled water | 4–10% by wt. |

According to a preferred embodiment to the present invention, the composition is the following:

| | |
|---|---|
| ammonium sulfoichthyolate | 1.5% by wt. |
| zinc oxide | 15% by wt. |
| titanium dioxide | 6% by wt. |
| fluid extract of Hamamelis | 1% by wt. | and the pharmaceutically acceptable carrier is present in the following percentages:

| | |
|---|---|
| anhydrous lanolin | 41.350% by wt. |
| white petrolatum | 13.670% by wt. |
| liquid paraffin | 15% by wt. |
| vanillin | 0.010% by wt. |
| essence of French lavender | 0.025% by wt. |
| distilled water | 6.445% by wt. |

This ointment has been employed for experimenting its therapeutic activity in treatment of paradentium diseases according to the following disclosure that is reported for exemplification purposes, and in almost all examined cases the product was shown to be of a remarkable efficiency, as such product caused full recovery from the disease or a clear improvement in the pathological conditions even with one only application of the composition.

THERAPEUTIC ACTIVITY

In the medical treatment of a case of dry pyorrhea, the ointment was spread as a layer of about 3 mm thickness on an oblong piece of cotton-wool previously wet with water, and said cotton-wool piece was applied between the lip and the gum at the point corresponding to the five teeth affected with pyorrhea. After 12 hours application in the night-time, which is the period of maximum quietness for the patient, the drug was removed and the complete disappearance was observed of the unsteadiness of teeth as well as a high strengthening of the same. Such strengthening regarded the first four teeth affected with pyorrhea, whereas the fifth tooth did not lose its mobility or unsteadiness. As said fifth tooth has started moving long before the other four teeth, it can be inferred that the application of the ointment according to the present invention is to be carried out short after the first symptoms of the disease arise. Indeed, the four teeth perfectly strengthened had started moving few weeks before the application of the medicament according to the present invention.

The subject undergoing the treatment did not show any side effects. The application of the composition caused tingling sensation just at the points corresponding to the teeth suffering from the disease.

Another subject showed reddened gums; he had a dental prosthesis and the contact with the same troubled him to the point of forcing him to remove the prosthesis from time to time.

Specially after a meal, the gum became inflammated and swollen. Surprisingly, after just one only application of the composition according to the present invention, the patient could comfortably keep his denture without incurring the vexing trouble he complained about.

A patient aged fiftyfive showed bleeding and swollen gums which were very sensitive to traumatisms even of a very low degree. He was to be cautious when brushing his teeth in order not to touch even lightly his gums, on pain of a troublesome bleeding. He made use systematically of mouth-washes with poor results.

After using the composition of the present invention, he could give up the use of mouth-washes, his gums did not bleed any more and that troublesome sensitivity disappeared completely.

Another subject has been affected with purulent alveolar pyorrhea for about sixteen months. Though his dentist urged him to undergo an incision operation on his gums, the subject refused such proposal and his condition became worse day by day.

He had recourse to the use of the commonly employed mouth-washes without any benefit even of a minimum extent. After one only application of the composition according to the present invention, a further check on the part of his dentist showed a very clear improvement. The purulent and swollen gums had become rose-colored and the purulent matter has disappeared completely.

Another case is that of a young man, aged twenty, who already was affected with a troublesome gingivitis with a high sensitivity and tendency to bleeding. Though the patient started employing regularly the commonly used mouth-washes, the inflammated and swollen state of his gums persisted.

After one application of the composition according to the present invention, said patient never complained about such trouble any more.

A woman, aged fifty, has been under treatment for some months with her dentist for a bad gingival inflammation with no appreciable results. At the moment when she had been subjected to the medical treatment with the composition according to the present invention, the patient despaired of getting better of such phlogosis, and she feared by that time for the safety of her teeth. Only after said treatment the disappearance was observed of all troubles, and the patient's gums, which were previously red and swollen, showed rose-colored and well vascolarized.

The cases observed, which were similar to those mentioned above, amount at the present time to several ten and just in two or three of them no remarkable success could be ascertained; moreover, no patient showed side effects.

The drug prepared employing the composition according to the present invention can be used, in addition to its form as an ointment, also as a lotion and as a powder, by varying the composition of the excipient in a suitable way.

The invention has been disclosed for exemplification purposes with reference to a particular embodiment of the same, but it is to be understood that those who are skilled in the art can make use of different modifications and changes of the same without departing from the spirit and scope of the invention for which protection is sought.

I claim:

1. A method for treating gingivitis and paradental pyorrhea, comprising topically applying a medicament composition comprising from 1% to 3% by weight of the ammonium salt of sulfoichthyolic acid, from 5 to 20% by weight of zinc oxide, from 3 to 9% by weight of titanium dioxide and from 0.5 to 2% by weight of a fluid extract of Hamamelis, in a pharmaceutically acceptable carrier.

2. A method according to claim 1 wherein said composition contains 1.5% by weight of the ammonium salt of sulfoichthyolic acid, 15% by weight of zinc oxide, 6% by weight of titanium dioxide and 1% by weight of a fluid extract of Hamamelis, in a pharmaceutically acceptable carrier.

3. A method according to claim 1 wherein said pharmaceutically acceptable carrier comprises anhydrous lanolin, white petrolatum, liquid paraffin, vanillin, essence of French lavender and distilled water.

4. A method according to claim 1, wherein said pharmaceutically acceptable carrier comprises from 35 to 45% by weight of anhydrous lanolin, from 10 to 20% by weight of white petrolatum from 10 to 20% by liquid paraffin, from 0 to 0.05% by weight of vanillin, from 0 to 0.06% by weight of essence of French lavender and from 4 to 10% by weight of distilled water.

5. A method according to claim 2, wherein said pharmaceutically acceptable carrier comprises 41.35% by weight of anhydrous lanolin, 13.67 by weight of white petrolatum, 15% by weight of liquid paraffin, 0.010% by weight of vanillin, 0.025% by weight of essence of French lavender and 5.445% by weight of distilled water.

6. A method according to claim 1, 2, 3, 4, or 5, wherein said medicament is in the form of an ointment.

* * * * *

UNITED STATES PATENT AND TRADEMARK OFFICE
CERTIFICATE OF CORRECTION

PATENT NO.  : 4,879,106

DATED       : November 7, 1989

INVENTOR(S) : Giorgio Voli

It is certified that error appears in the above-identified patent and that said Letters Patent is hereby corrected as shown below:

Column 6 line 4, change  " 5.445% by " to -- 6.445% by --

Signed and Sealed this

Fifth Day of November, 1991

*Attest:*

HARRY F. MANBECK, JR.

*Attesting Officer*     *Commissioner of Patents and Trademarks*